US00PP27637P2

(12) United States Plant Patent
Probst

(10) Patent No.: US PP27,637 P2
(45) Date of Patent: Jan. 31, 2017

(54) ***COREOPSIS* PLANT NAMED 'SUNSPLASH'**

(50) Latin Name: ***Coreopsis* hybrid**
Varietal Denomination: Sunsplash

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 268 days.

(21) Appl. No.: 14/120,965

(22) Filed: Jul. 16, 2014

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — June Hwu
(74) *Attorney, Agent, or Firm* — Penny J. Aguirre

(57) ABSTRACT

A new cultivar of hybrid *Coreopsis* plant named 'Sunsplash' that is characterized by its compact plant habit reaching about 30 cm in height and 50 cm in spread, its prolific blooming habit from mid June until frost in Connecticut, its large inflorescences with ray florets that are bright red in color with gold streaks near the apex with the coloration retained throughout the growing season, and its relatively sterile inflorescences when grown under typical garden conditions and lack the need for deadheading of spent blooms for continuous bloom.

2 Drawing Sheets

Botanical classification: *Coreopsis* hybrid.
Variety denomination: 'Sunsplash'.

CROSS REFERENCE TO A RELATED APPLICATION

This application is co-pending with a U.S. Plant Patent Application filed for a plant derived from a similar cross in the Inventor's breeding program that is entitled *Coreopsis* Plant Named 'Daybreak' (U.S. Plant Pat. No. 27,138).

BACKGROUND OF THE INVENTION

The present invention relates to a new and distinct cultivar of *Coreopsis* plant, botanically of hybrid origin and known as *Coreopsis* 'Sunsplash' and will be referred to hereinafter by its cultivar name, 'Sunsplash'. The new cultivar of *Coreopsis* is an herbaceous perennial grown for landscape and container use.

The new Invention arose from an ongoing controlled breeding program in Hubbardston, Mass. The objective of the breeding program is to develop hybrid cultivars of *Coreopsis* with unique and superior garden attributes. In particular, to develop cultivars that are long-lived, sturdy, exhibit a true perennial habit and cold hardy to at least U.S.D.A. Zone 5 in a wide range of flower colors and plant forms.

The Inventor made a controlled cross in July of 2009 in his test garden in Hubbardston, Mass. between an unnamed plant from his breeding program, ref. no. Q1 07-1, as the female parent and pollen that was pooled from a variety of unnamed plants from his breeding program as the male parent (all nearly sterile). The exact characteristics of the pollen parent are therefore unknown. 'Sunsplash' was selected in September of 2010 as a single unique plant amongst the resulting seedlings.

Asexual propagation of the new cultivar was first accomplished by stem cuttings under the direction of the Inventor in Kensington, Conn. in September of 2010. Asexual propagation by stem cutting has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Sunsplash' as a unique cultivar of *Coreopsis*.

1. 'Sunsplash' exhibits a compact plant habit reaching about 30 cm in height and 50 cm in spread.
2. 'Sunsplash' exhibits a prolific blooming habit from mid June until frost in Connecticut.
3. 'Sunsplash' exhibits large inflorescences with ray florets that are bright red in color with gold streaks near the apex with the coloration retained throughout the growing season.
4. 'Sunsplash' is relatively sterile when grown under typical garden conditions and does not require deadheading of spent blooms for continuous bloom.

The female parent of 'Sunsplash', Ref. No. Q1 07-1, differs from 'Sunsplash' in being highly fertile and produces full seed heads that result in a one month blooming period without deadheading. 'Sunsplash' can be most closely compared to *Coreopsis* cultivars 'Cosmic Eye' (U.S. Plant Pat. No. 22,601) and 'Daybreak'. 'Cosmic Eye' is similar to 'Sunsplash' in having a compact plant habit and in having large flowers. 'Cosmic Eye' differs from 'Sunsplash' in having ray florets that are bright yellow in color with a burgundy eye. 'Daybreak' is similar to 'Sunsplash' in having a compact plant habit and in having red ray florets. 'Daybreak' differs from 'Sunsplash' in having inflorescences with ray florets that are primarily gold in color with the red eye expanding out to the apex and edges when night temperatures are cool at the end of the growing season, while the red coloration of 'Sunsplash' is retained throughout the growing season.

BRIEF DESCRIPTION OF THE DRAWINGS

The accompanying colored photographs illustrate the overall appearance and distinct characteristics of the new *Coreopsis*.

The photograph in FIG. 1 was taken of a 9 month-old plant of 'Sunsplash' as grown outdoors in a one-gallon container in Kensington, Conn. and shows the overall growth and flowering habit of 'Sunsplash'.

Figure 1:
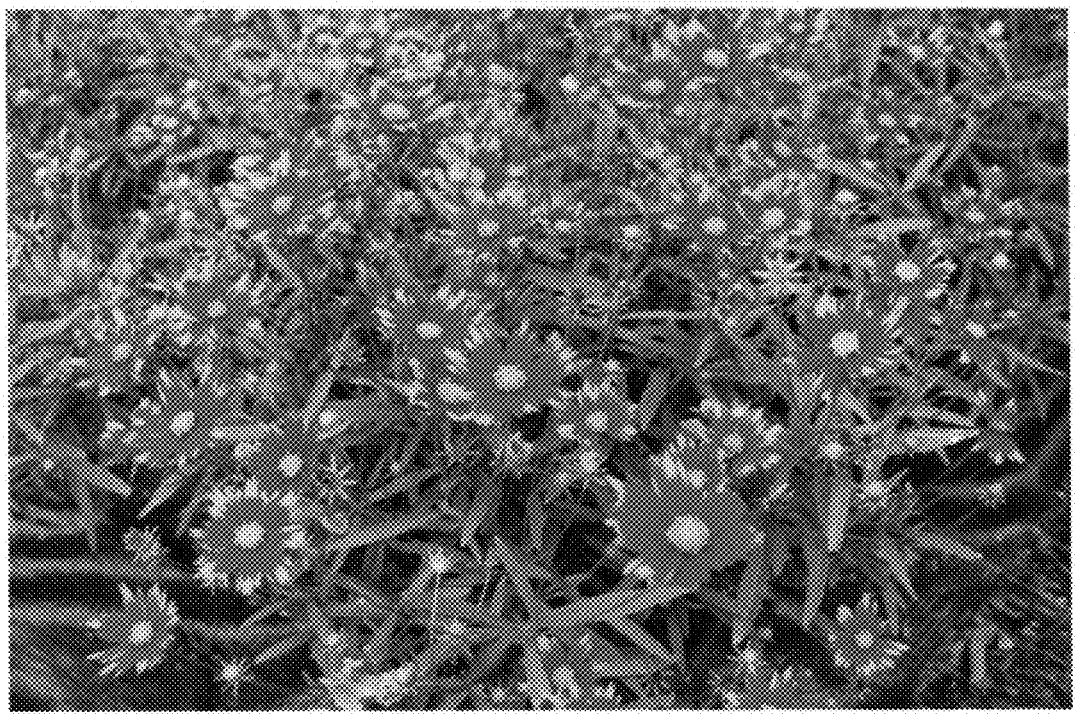
Figure 2:
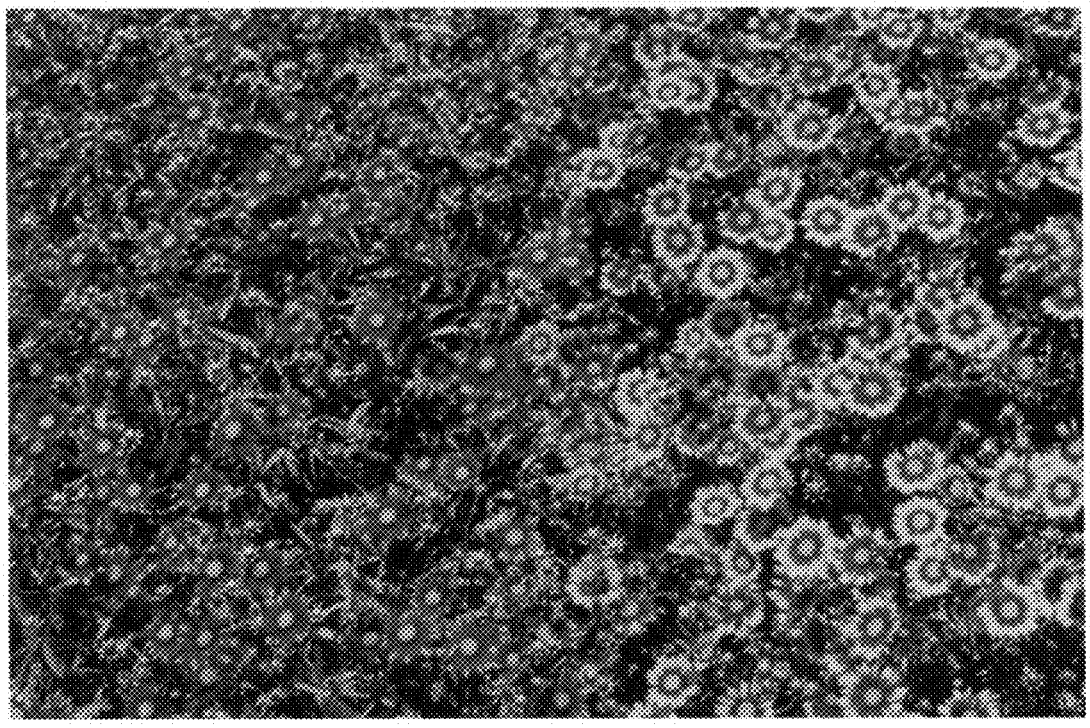

The photograph in FIG. 2 was taken of 18 month-old plants after overwintering in one-gallon containers in Kensington, Conn. and provides a comparison between 'Daybreak' on the right and 'Sunsplash' on the left.

The colors in the photograph may differ slightly from the color values cited in the detailed botanical description, which accurately describe the colors of the new *Coreopsis*.

DETAILED BOTANICAL DESCRIPTION

The following is a detailed description of the new cultivar as observed for four years in a trail garden in Hubbardston, Mass. with the detailed botanical data collected from six month-old plants of the new cultivar as grown in one-gallon containers in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

- *Blooming period.*—Blooms from mid June until frost in Connecticut.
- *Plant habit.*—Herbaceous perennial, clump-forming, compact, low growing leafy stems with flowering stem held above the foliage.
- *Height and spread.*—Reaches 30 cm in height in blooms, spreads to about 50 cm.
- *Cold hardiness.*—At least to U.S.D.A Zone 5.
- *Diseases resistance.*—More resistance to powdery mildew has been observed in comparison to *Coreopsis grandiflora* cultivars grown under the same conditions.
- *Root description.*—Fibrous, fine and well branched.
- *Propagation.*—Terminal stem cuttings and division.
- *Growth rate.*—Vigorous but retaining a compact habit.

Stem description:

- *Shape.*—Oval, solid.
- *Stem color.*—Young; 144A, mature; a blend of N137B and 137C.
- *Stem size*—Main stem (including peduncles) averages 7 cm in length and 1 cm in width with lateral branches an average of 6 cm in length and 2 mm in width.
- *Stem surface.*—Glabrous when young, ridged and glabrous when mature.
- *Branching habit.*—An average of 7 basal branches with 6 secondary branches, branch internode is variable but typically about 3 cm and arise opposite at nodes.

Foliage description:

- *Leaf division.*—Simple.
- *Leaf margins.*—Entire and slightly undulate, primarily unilobate and occasionally trilobate.
- *Leaf size.*—Trilobate leaves; up to 4.5 cm in length and 2 cm in width when mature with center lobe an average of 4.5 cm in length and 5 mm in width and secondary lobes an average of 2 cm in length and 3 mm in width, unilobate leaves; an average of 7 cm in length and 1 cm in width.
- *Leaf shape.*—Unilobate leaves; lanceolate, trilobate leaves; deltoid in overall shape with lanceolate lobes.
- *Leaf base.*—Attenuate.
- *Leaf apex.*—Narrowly acute.
- *Leaf venation.*—Pinnate, not prominent, coloration same as leaf on both surfaces.
- *Leaf attachment.*—Sessile.
- *Leaf arrangement.*—Opposite.
- *Leaf surface.*—Upper and lower surface glabrous and dull.
- *Leaf color.*—Young and mature upper surface; 137A, young and mature lower surface; 147B.

Flower description:

- *Inflorescence type.*—Composite with ray florets surrounding disk florets in the center, forming a radiant head, inflorescences are borne on terminals arising from leaf axils.
- *Lastingness of inflorescence.*—About 8 to 10 days until senescence of ray florets, bracts and disk florets are persistent.
- *Fragrance.*—Faint.
- *Quantity of inflorescences.*—An average of 6 per lateral branch, an average of 60 per plant grown in a one-gallon container.
- *Inflorescence size.*—Up to 1.3 cm in depth and up to 5 cm in diameter with disk portion up to 1.1 cm in diameter.
- *Inflorescence buds.*—Average of 6 mm in depth and 8 mm in diameter, shape is spherical, color is a blend of 15A and slight overlay of 165B.
- *Peduncle.*—Strong, average of 9 cm in length and 1 mm in diameter, 146A in color, glabrous surface.

Involucral bracts:

- *Bract number.*—Two rows of 8.
- *Bract arrangement.*—Un-fused with outer bracts somewhat reflexed when flower is fully open and becoming horizontal after ray florets drop.
- *Bract size.*—Outer bracts; up to 7 mm in length and 2 mm in width, inner bracts; average 5 mm in length and 3 mm in width.
- *Bract color.*—138A on both surfaces of outer bracts and 146A on both surfaces of inner bracts.
- *Bract texture.*—All surfaces glabrous.
- *Bract apex.*—Acute.
- *Bract base.*—Truncate.
- *Bract margins.*—Entire.
- *Bract shape.*—Lanceolate.

Ray florets (pistillate):

- *Number.*—8 per inflorescence.
- *Shape.*—Oblanceolate, appearance of three longitudinal sections with center section longer and apex of each free.
- *Size.*—Up to 2.2 cm in length and 1.3 cm in width.
- *Apex.*—3-lobed with center lobe pointed emarginate and side lobes pointed.

*Base.*—Cuneate.

*Margins.*—Entire on sides, lobed at apex.

*Aspect.*—Held slightly cupped upward.

*Texture.*—Velvety on upper surface and glabrous on lower surfaces.

*Color.*—Inner surface when opening; base 187A, mid section 185A, mid section to tip is 17A, outer surface when opening; a blend of 21A and 11A, upper surface when fully open; a blend of 187A and 46B, tip 17A, lower surface when fully open; 17A blended with streaks of 46A from the base to the mid section.

Disk florets (perfect):

*Number.*—An average of 90 per inflorescence.

*Shape.*—Tubular, corolla is fused, flared at apex.

*Size.*—About 5 mm in length and 1 mm in width.

*Color.*—En masse; 18A, corolla; base (tube) is 18B in color, flared portion is 17A and translucent.

*Receptacle.*—About 7 mm in diameter and 3 mm in depth, 1C in color.

Reproductive organs:

*Presence.*—Disk florets are perfect, ray florets are pistillate.

*Gynoecium.*—1 Pistil, 4 mm in length, style is very fine and about 11A in color and translucent, bifid pilose stigma is 23A in color with branches about 1 mm in length and recurved, ovary is 2 mm in length, 4 mm in width, inferior, and 145B.

*Androcoecium.*—5 stamens, fused into tube surrounding style, 2 mm in length and 0.5 mm in width, about 200B in color, no pollen was observed.

*Fruit/seed.*—No fruit or seed development was observed, observed to be relatively sterile.

It is claimed:

1. A new and distinct cultivar of *Coreopsis* plant named 'Sunsplash' as herein illustrated and described.

* * * * *